(12) United States Patent
Cocks et al.

(10) Patent No.: US 8,396,669 B2
(45) Date of Patent: Mar. 12, 2013

(54) ANALYSIS SYSTEM AND PROCEDURES

(75) Inventors: Stephen James Cocks, Glen Iris (AU); Chris Zawadzki, Knoxfield (AU)

(73) Assignee: Leica Biosystems Melbourne Pty Lt, Mount Waverley (AU)

( * ) Notice: Subject to any disclaimer, the term of this patent is extended or adjusted under 35 U.S.C. 154(b) by 1331 days.

(21) Appl. No.: 10/546,458

(22) PCT Filed: Feb. 23, 2004

(86) PCT No.: PCT/AU2004/000226
§ 371 (c)(1),
(2), (4) Date: Jun. 16, 2006

(87) PCT Pub. No.: WO2004/074845
PCT Pub. Date: Sep. 2, 2004

(65) Prior Publication Data
US 2006/0265133 A1    Nov. 23, 2006

(30) Foreign Application Priority Data
Feb. 21, 2003   (AU) .................................. 2003900780

(51) Int. Cl.
*G01N 33/48* (2006.01)
(52) U.S. Cl. ......................................................... 702/19
(58) Field of Classification Search ...................... 702/19
See application file for complete search history.

(56) References Cited

U.S. PATENT DOCUMENTS

| 5,948,359 A | 9/1999 | Kalra et al. |
| 6,352,861 B1 | 3/2002 | Copeland et al. |
| 6,461,570 B2 | 10/2002 | Ishihara et al. |
| 2003/0111494 A1* | 6/2003 | Lin et al. ........................ 222/505 |
| 2004/0005714 A1* | 1/2004 | Safar et al. ...................... 436/43 |
| 2004/0014067 A1* | 1/2004 | Lyamichev et al. .............. 435/6 |
| 2004/0033163 A1* | 2/2004 | Tseung et al. ................... 422/63 |

FOREIGN PATENT DOCUMENTS

| EP | 0 867 724 A2 | 9/1998 |
| EP | 1102068 A1 | 5/2001 |
| JP | 8-94624 | 4/1996 |
| JP | 8262029 | 10/1996 |
| JP | 8334515 | 12/1996 |
| JP | 20011074752 | 3/2001 |
| WO | WO 01/51909 A1 | 7/2001 |
| WO | WO 0168259 A1 | 9/2001 |

OTHER PUBLICATIONS

Pemberton, "Managing the Details of Compound Library Production," American Laboratory (Jul. 2001) pp. 18 and 20-23.*

* cited by examiner

*Primary Examiner* — Jerry Lin
(74) *Attorney, Agent, or Firm* — Sughrue Mion, PLLC

(57) ABSTRACT

A system and apparatus for automation of microscope slide sample staining is disclosed. The slides are labelled with a unique identification, preferably a machine readable code printed onto a label, where the label is affixed to the slide. The label is a pointer to information in a database containing patient data on the sample, including staining protocol and reagents to be applied. Also disclosed is a reagent identification system where reagent containers used in the above staining system having a unique package identifier, preferably in the form of a label having a machine readable code. Data relating to the contents of the reagent containers, such as volume, batch number, reagent type and expiry date, is stored in a database in association with the unique package identifier. Using the reagent container unique package identifier it is possible to associate the type of protocol, and precise reagent used in the test with the patient data, allowing tracking of the test applied to the sample.

11 Claims, 17 Drawing Sheets

Database screenshot

ANALYSIS SYSTEM AND PROCEDURES

FIELD OF THE INVENTION

The present invention relates to instruments and apparatus used laboratory equipment used for research and diagnostic purposes in the medical field.

BACKGROUND OF THE INVENTION

Staining tissue specimens on a microscope slide is commonly undertaken to detect disease and abnormality, as well as for research purposes. The specimens on the microscope slide are usually thin cross sections of human tissue, and without appropriate treatment, elements of interest in the specimen are not distinguishable from other elements. In immunohistochemistry, antibodies are applied to the specimen to determine whether antigens are contained within the specimen, and also to determine the level of antigens. A stain and counterstain are usually used to indicate the areas where antibodies have bound. It is usually necessary to prepare the specimen before applying the antibodies to ensure adequate and consistent binding and staining.

In immunohistochemistry, often it is not only the detection of an antigen that is important, but also the level of antigen expression on the specimen, making consistency of binding and staining a prime concern. Similar concerns also occur with insitu hybridisation.

Preparation of the specimen and application of the antibody, and stain, if performed to a predetermined recipe, called a protocol. Each specimen undergoing a test will have a predetermined protocol for application of the antibody. There are a large number of antibodies and a number of different protocols that may be applied to each antibody, depending on the test selected, and therefore it is crucial that the correct protocol and antibody be applied to the specimen. Not only is it important to minimise errors in Immunohistochemistry, and other related processes, but it is also important to be able to detect when a mistake has been made.

The above is also true of in-situ hybridisation tests, which may be undertaken on the same instrument as immunohistochemistry, and is also used to detect disease.

SUMMARY OF THE INVENTION

In accordance with one aspect of the present invention there is provided a method of identifying a slide including:
Applying a unique indicator to a slide
Where the unique identifier is associated with a database holding sample identification and test information.

In one form the test information contains the protocol and primary antibody to be applied to the sample.

In accordance with another aspect of the present invention there is provided a method of identifying a reagent container including:
Applying a unique indicator to a container
Where the unique identifier is associated with a database holding data on the reagent within the container.

In accordance with one aspect of the invention, there is provided an analysis system, including:
analysis system having a reader for reading identifiers which uniquely identify respective sample receptacles and reagent containers and a controller that receives input from the reader and applies reagent from the containers to the receptacles, in accordance with separately input test protocol information.

Preferably, the system includes the sample receptacles and reagent containers, with the identifiers applied thereto.

Preferably, the system includes data storage for storing reagent information and sample information. More preferably, the sample information includes the test protocol information.

Preferably, the reagent information is read from a sequence of characters that are provided on a tag applied relative to the associated reagent container, wherein the sequence includes embedded identifier code to allow the product information to be cross-correlated with an associated one of the identifiers.

Most preferably, the identifier and sequence are both in the form of barcodes and the identifier barcode is preferably of larger dimension, relative to the sequence code, to facilitate easier reading by the reader.

In another aspect, there is provided an identification system, including:
a tag for identifying a reagent, wherein the tag is provided with a sequence of characters having reagent information which is adapted to be read into a data storage; and
an identifier which is applied relative to the reagent, to uniquely identify a reagent container, wherein the identifier is arranged to be read separately of the sequence.

Preferably, the sequence includes embedded identifier code to allow the reagent information to be cross-correlated with the identifier.

Preferably, the identifier is provided on the tag.

Preferably, the identifier is formed of similar-type characters to those forming the sequence.

Preferably, the identifier is formed of less characters, compared to the sequence and the characters of the identifier are of larger dimensions relative to the sequence characters, to facilitate easier reading.

Preferably, the sequence and identifier are provided in the form of barcodes.

Preferably, the tag is applied to the reagent container.

In another aspect, there is provided a testing procedure including:
reading an identifier which uniquely identifies a sample;
separately establishing a test protocol, for application to the sample;
reading an identifier which uniquely identifies a reagent; and
conducting the test protocol.

In another form the present invention relates to a testing procedure including:
reading an identifier which uniquely identifies a sample;
separately establishing a test protocol, for application to the sample;
reading an identifier which uniquely identifies a reagent; and
conducting the test protocol.

In another form the present invention relates to a method of identifying a slide including:
Applying a unique indicator to a slide
Where the unique identifier is associated with a database holding sample identification and test information.

In another form the present invention relates to a method of identifying a reagent container including:
applying a unique indicator to a container
Where the unique identifier is associated with a database holding data on the reagent within the container.

In another form the present invention relates to a method of dispensing reagent from a testing apparatus including holding information in a database relating to the reagent,
Said information including reagent type, reagent expiry date and initial reagent volume, and a unique package identifier including the steps of scanning all reagent containers in the test apparatus before dispensation
and where a reagent is required to be dispensed from a reagent container and there are two or more of the same type of container on the test apparatus, referring to the information in the database to make a decision as to which reagent to dispense.

Preferably the decision is based on expiry date of the reagent containers such that the reagent container with the nearest expiry date is used first.

In another form the present invention relates to a method of determining the dispensation of a reagent from a reagent container during tests run in a test apparatus including
entering data into a database, said data including reagent type, reagent expiry date and initial reagent volume, and a unique package identifier for each container;
including the steps of scanning all reagent containers in the test apparatus before dispensation;
determining the amount of reagent remaining in each container scanning the slides to determine the amount of reagent required to complete the tests In another form the present invention relates to a method of operation including:
Entering patient data into control system sample database, said patient data including data identifying the sample and test to be applied to the sample
Wherein reagent container are registered in the database, registration data including reagent type, volume of container,
Printing Labels for each slide to be tested and applying labels to respective slides
Loading slides into apparatus
Scanning slides to determine the unique sample identifiers of each slide
Querying sample database to determine protocols to be applied to each slide loaded into apparatus
Scanning reagent containers loaded into the apparatus
Querying reagent database to determine type, and volume remaining in reagent containers
Determining dispensation of reagent onto slides on the basis of information in the reagent database.

Preferably data from a test is sent from the test apparatus to the slide database.

In another form the present invention relates to a method of determining test data for a slide that has been tested on a test apparatus including
Placing a unique sample identifier on a slide
Entering data into a patient database including test information relating to a protocol
Loading the slide into the apparatus
Scanning the slide to determine the unique sample identifier
Querying the sample database for the test data associated with the unique sample identifier
Performing the test on the slide according to the protocol in the sample database
Sending information to the sample database describing the test actually applied to the sample on the slide.

In another form the present invention relates to a label for a reagent container having a first identifier including a unique slide identifier and a second identifier containing information regarding the contents of the container.

BRIEF DESCRIPTION OF THE DRAWINGS

The invention is more fully described, by way of non-limiting example only, with reference to the accompanying drawings, in which.

DETAILED DESCRIPTION OF THE PREFERRED EMBODIMENTS

Figure 1:
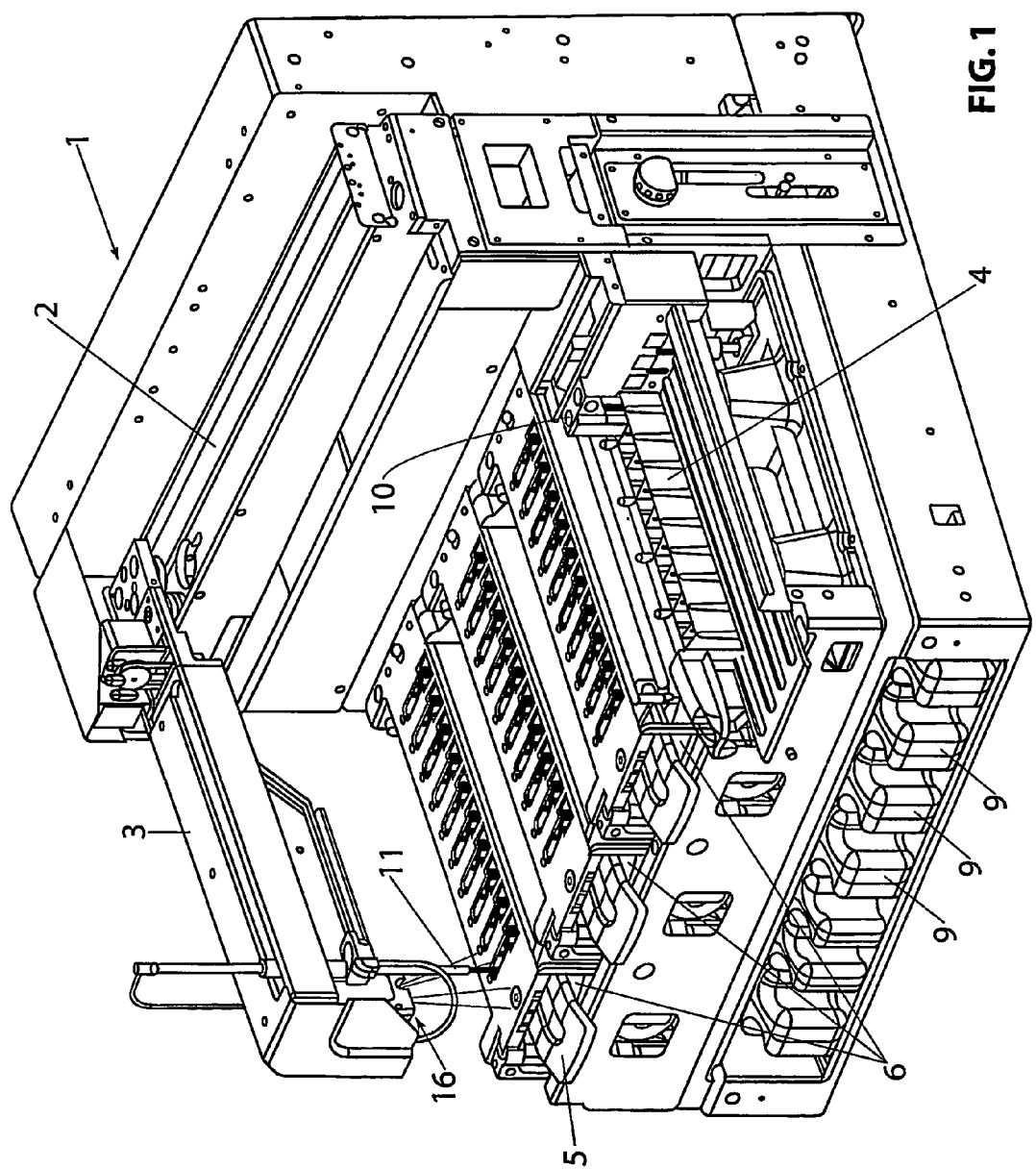
FIG. 1 is a perspective view of a module of a test system.
Figure 2:
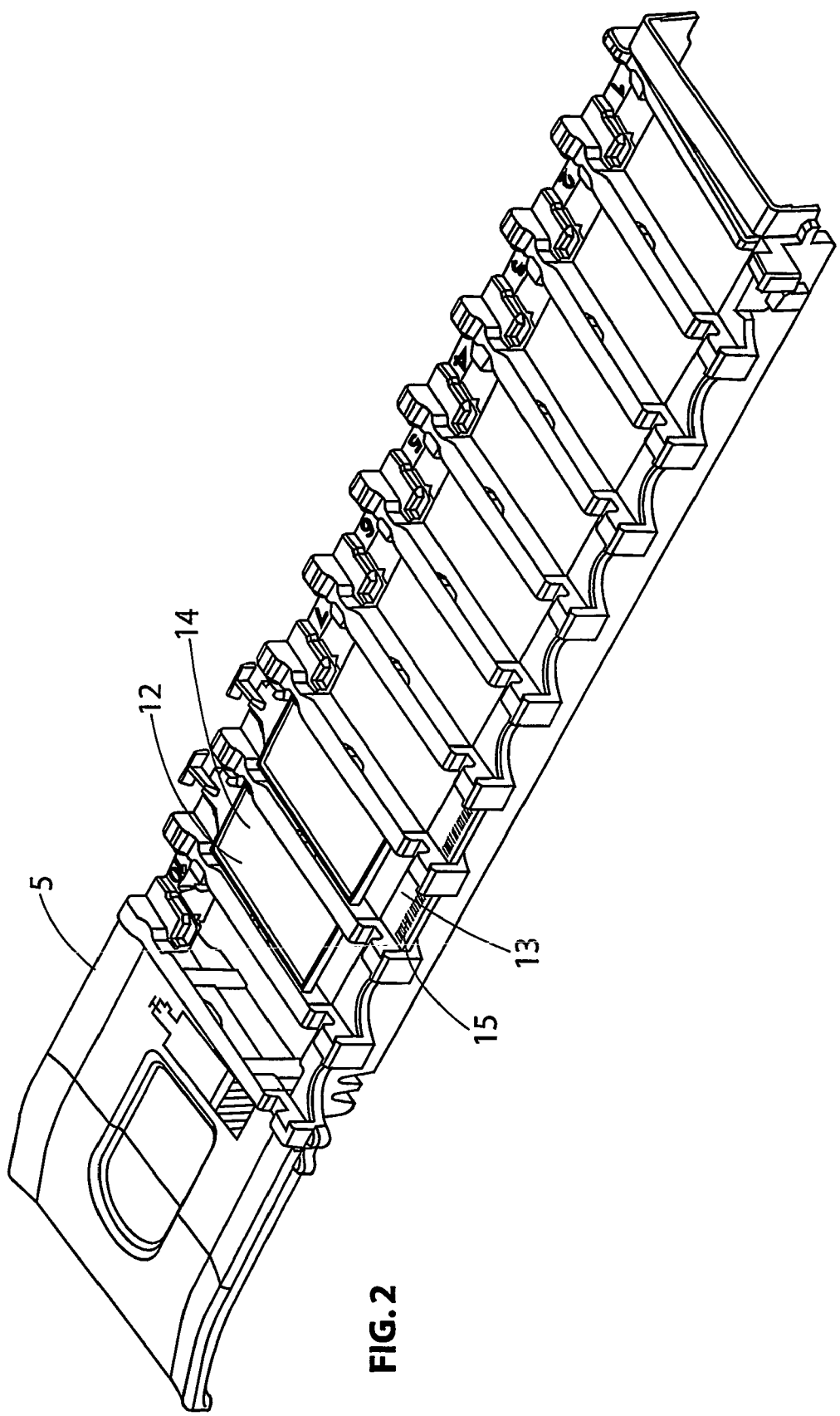
FIG. 2 is a perspective view of a sample tray.
Figure 7:
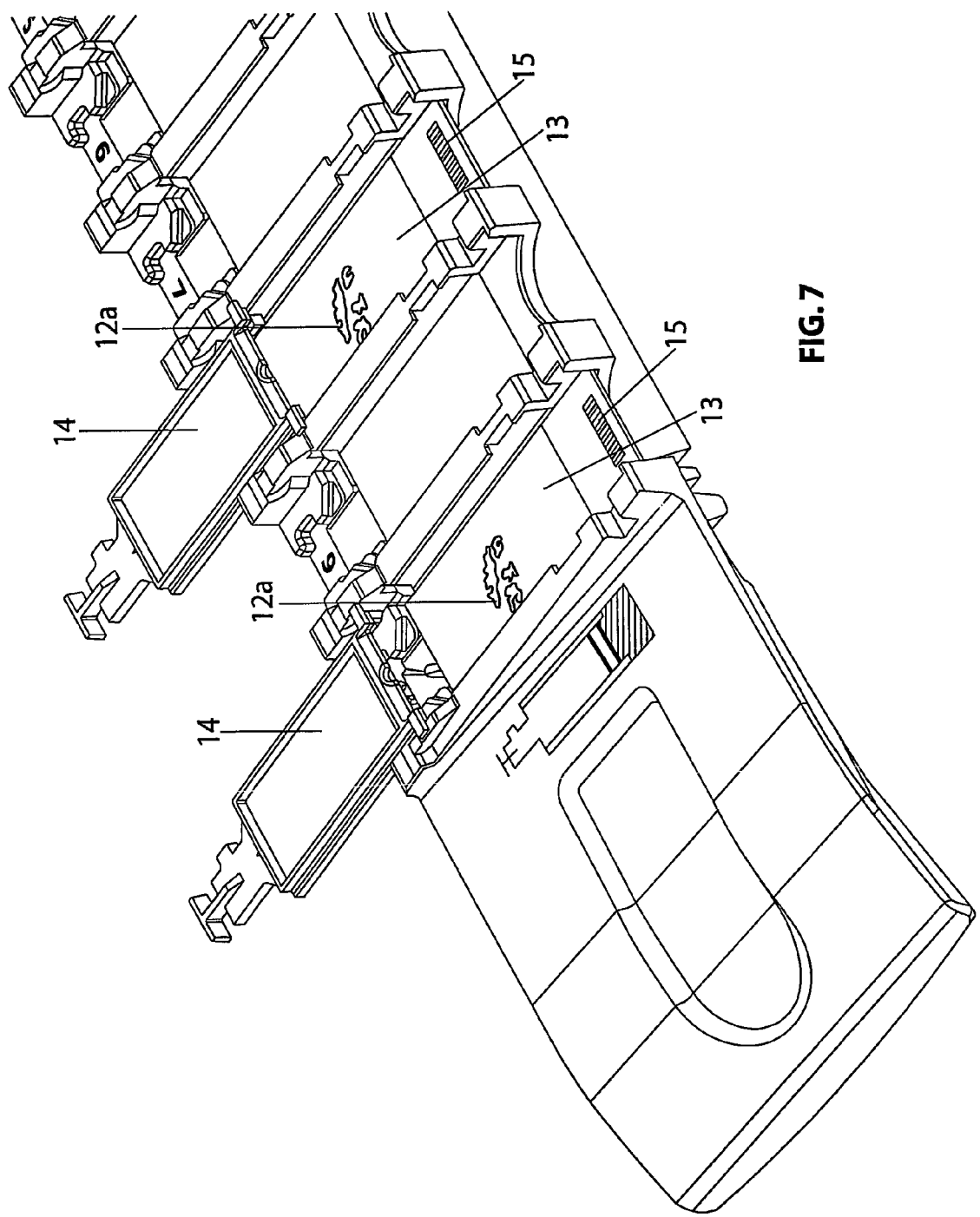
FIG. 7 is a perspective view of a tray holding slides having samples and unique sample identifiers.
Figure 8:
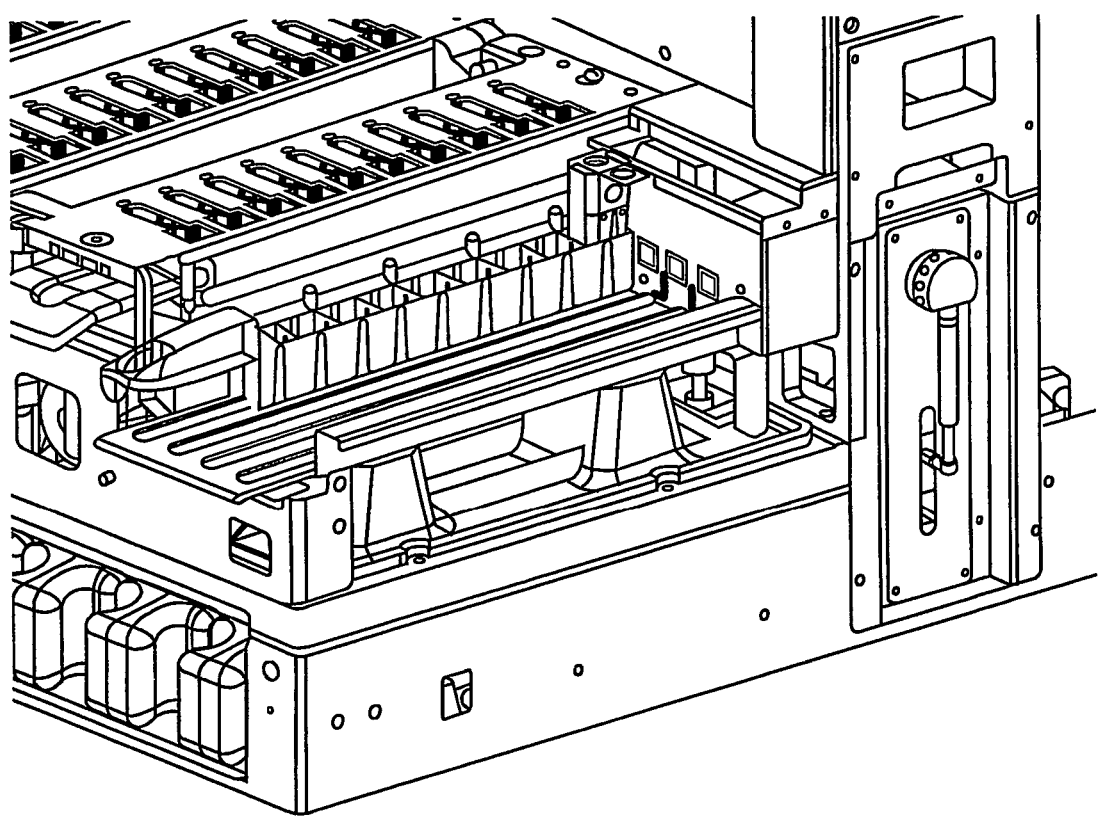
FIG. 8 is a perspective view of a module of a test system showing a reagent tray and reagent container.

An analysis system 1 is shown in FIG. 1 as including a test system such as processing module 2, which in this embodiment is a Bond-X® instrument manufactured by the applicant/assignee Vision BioSystems Ltd of Australia. The processing module 2 includes a robotic arm 3 having a probe 11 for transferring reagent from reagent containers 10 in tray 4 to sample receptacles 12 in tray 5, as shown in FIG. 2. There are three trays 5 shown in FIG. 1 loaded into receiving zones 6, each holding ten sample receptacles 12 in the form of microscope slides 13. The robotic arm 3 moves in the X-Y direction, and contains a probe 11 able to move in the Z direction to remove reagent from the containers 10 and dispense to samples 12a on slides 13. The arrangement of the slides 13 in tray 5 is shown in more detail in FIG. 7.

Bulk reagent containers 9 may contain either bulk reagents such as distilled water, buffer solution, or may be used to store waste fluid. The probe 7 is connected via fluid lines 7a to a syringe style pump to accurately withdraw and dispense reagent from containers 10. While only one container 10 is shown in tray 4, there may be up to 9 containers in the tray 4, in the present embodiment, and up to four trays in the module. Fluids may also be drawn from the bulk reagent containers 9 using internal plumbing connections (not shown) in the apparatus 2 connected to the probe 11. An optical information reader 16 is included on the robotic arm 3, and its operation is discussed below.

Also contained within the processing module 2 is a controller (not shown) used to control the robot arm and other functions of the apparatus. Typically the controller is a computer having cpu, memory, storage such as a hard drive, network devices, peripheral controllers for controlling pumps and the robot arm as necessary, and other features typical of a computer used to control the processing module 2.

The processing module 2 may contain additional elements such as slide supports that incorporate heaters, drainage means for the slides, covertile manipulators and fans for assisting in drainage of the reagent from the slides. Further details are described in Patent application No. WO2004/001390 and WO2004/001389, the contents of which are incorporated by reference. Also incorporated are the contents of Australian Provisional Patent Application No. 2003900810 titled Method of Scheduling.

In use, a slide 13 will be prepared with a patient tissue sample. Typically this involves obtaining a sample of the patient material, such as a tissue biopsy, preparing the material (embedding in wax), and placing it on the slide. In the present embodiment, the slide will be identified using a unique slide label identifier (USLI) 15, typically printed onto a label and placed onto the slide.

In the first example, the slide label is printed after patient data has been entered into the database, however the label may be printed beforehand as described below.

An example of a data entry method and apparatus is disclosed below.

Description of Software Operation.

The GUI software runs on Windows XP and uses the familiar button layout with pop up windows where data may be entered. Screen shots have been captured to assist in the description of the system.

The following is a sequence of events to register a slide so that the Bond-X system will recognise the slide automatically once placed in a tray and loaded into the instrument.

Sequence for Adding Patient and Slide Details to the Bond-X System

Step 1: ADD CASE

Figure 11:
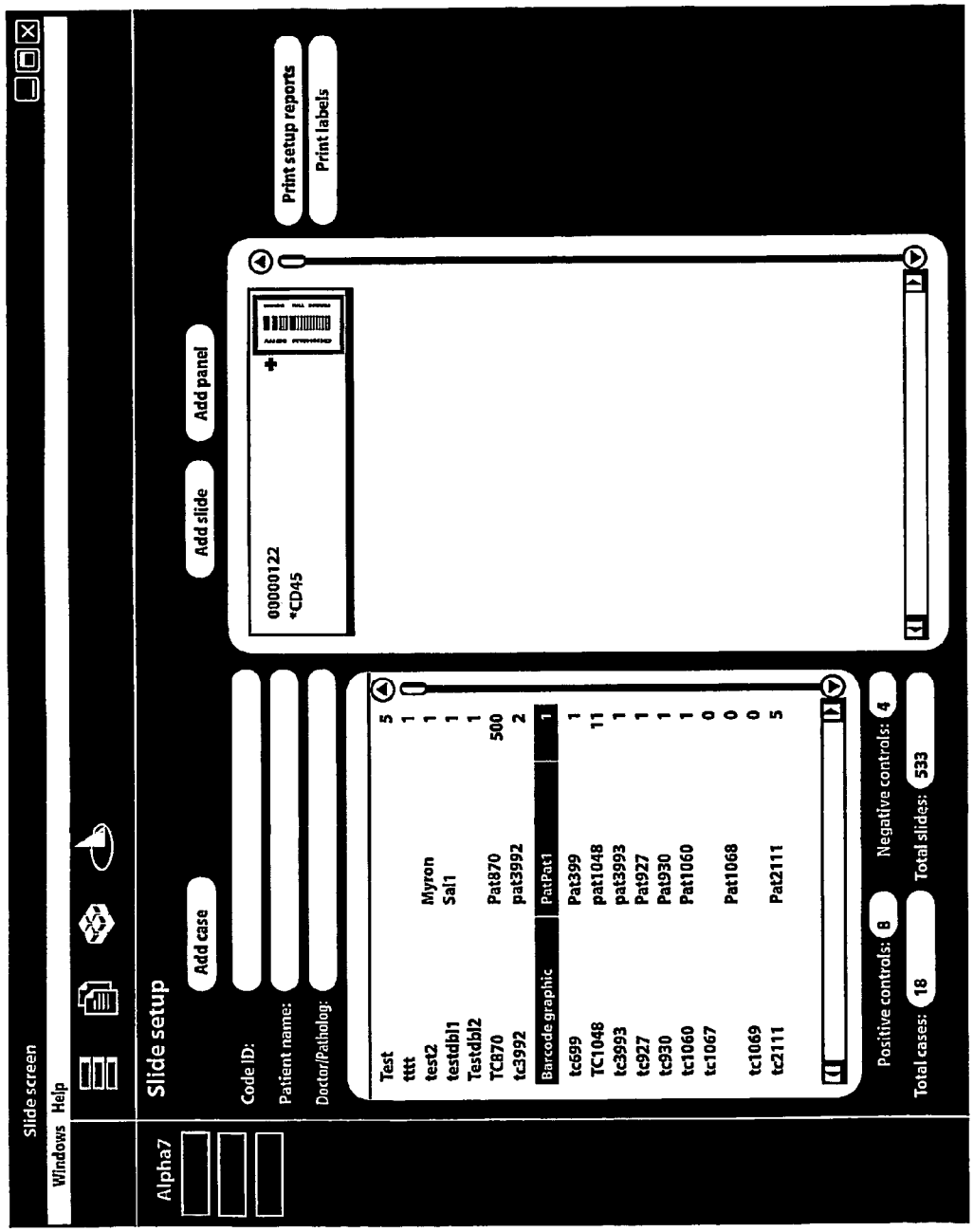
FIGS. 11-17 are screen shots from the user interface of the analysis system.

Patient information for the sample is entered into the database by clicking the ADD CASE button. A pop-up window appears and the following data can be added: Patient Name, Doctor Name and Case Id. This information, once accepted, is shown in the list in Window 1 of FIG. 11.

Figure 5:
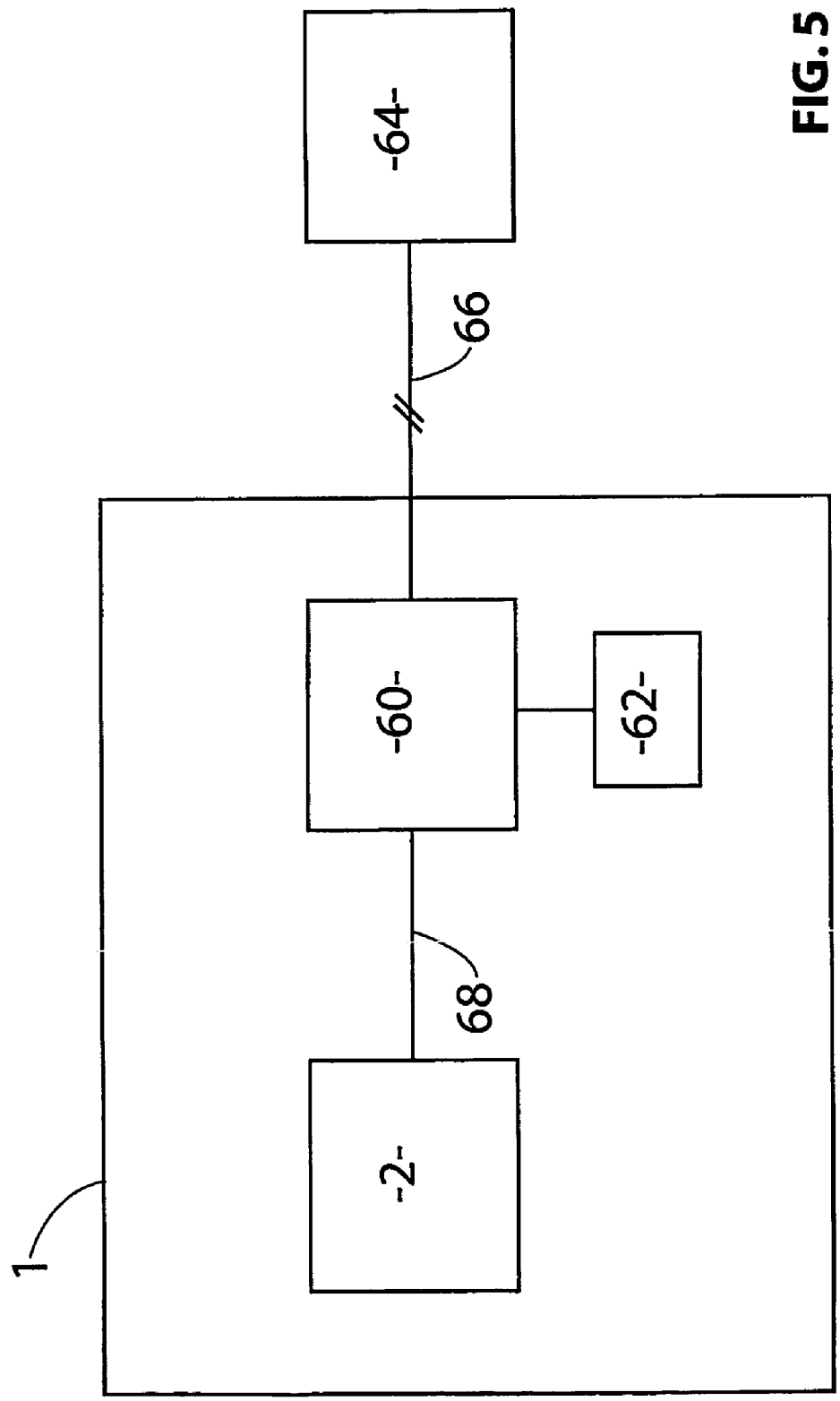
FIG. 5 is schematic of the layout of the test system.
Figure 6:
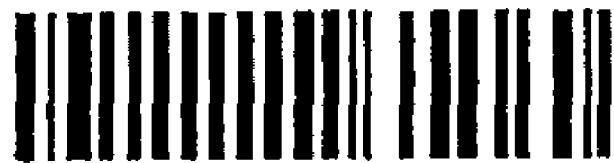
FIG. 6 shows an of a unique sample identifier.

Case details are shown in Window 1, and stored in a database on the controlling computer. Alternatively, data maybe imported from an external database 90, such as a separate hospital or doctor's database 64 over a network connection 66 or other connection, as shown in FIG. 5, rather than added manually.

Other information may be input using the ADD SLIDE and ADD PANEL buttons, and these will be described below.

Step 2: ADD SLIDE

Figure 12:

When samples from a patient are mounted onto slides, and those slides are to have tests performed upon them by the analysis system, then the details of each slide must be entered. To enter slide details, a case is chosen from those already entered (as shown by the darkened field in Window 1), and the Add SLIDE button is selected. This allows the operator to register a number of different slides all connected to a particular CASE ID. When the ADD SLIDE button is pressed, Window 2 of FIG. 12 appears. Already pre-entered into Window 2 is SLIDE ID, Patient Name, and Case ID. SLIDE ID is a unique number from the database, and is chosen sequentially from the end of a list of previous slide identifiers. Thus, every slide can be uniquely identified by its own slide number.

To the right of the slide id section, a Bar Code can be seen, which is a representation of the USLI. USLI's are obtained sequentially from the database, and contain no other information than a pointer in the database to the slide id The Slide Type has been pre-selected by the instrument, as has the Staining Mode (volume of application of fluid to the slide). Alternatively, the user may choose their own slide type from the list provided.

Thus, in this embodiment, when the Bar Code 50 is generated, the instrument has no way of knowing what reagents are to be applied to the slide. Further, the Bar Code 50 does not change as long as the window is open, that is, it does not change when a Primary/Staining Protocol is selected, or changed from a previous reagent, provided the bar code has not been invalidated.

Figure 13:

Window 3 of FIG. 13 shows the Primary and Staining Protocol having been selected. The Bar Code is still the same.

The bar code is then printed.

Figure 14:

If the Staining Protocol, Primary, case details are changed after printing (in this case from Bond™ IHC Protocol 01 to Bond™ IHC Protocol 02), then the bar code is invalidated and a new different bar code is generated using the same method as for the original generation. The newly selected Staining Protocol is shown in Window 5 of FIG. 14. As the changes have not been accepted into the system yet, the Bar Code has not changed.

Figure 15:
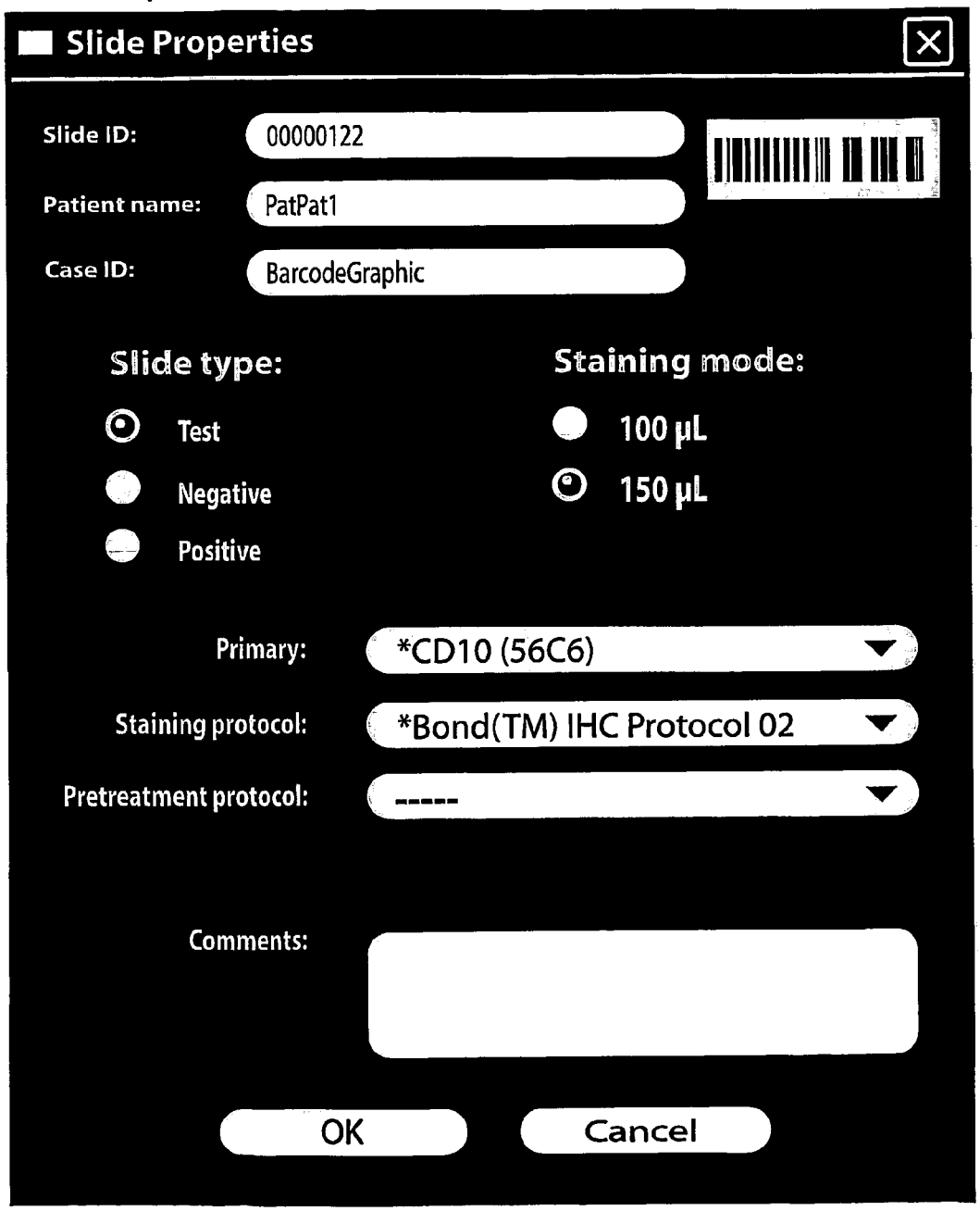
Figure 16:
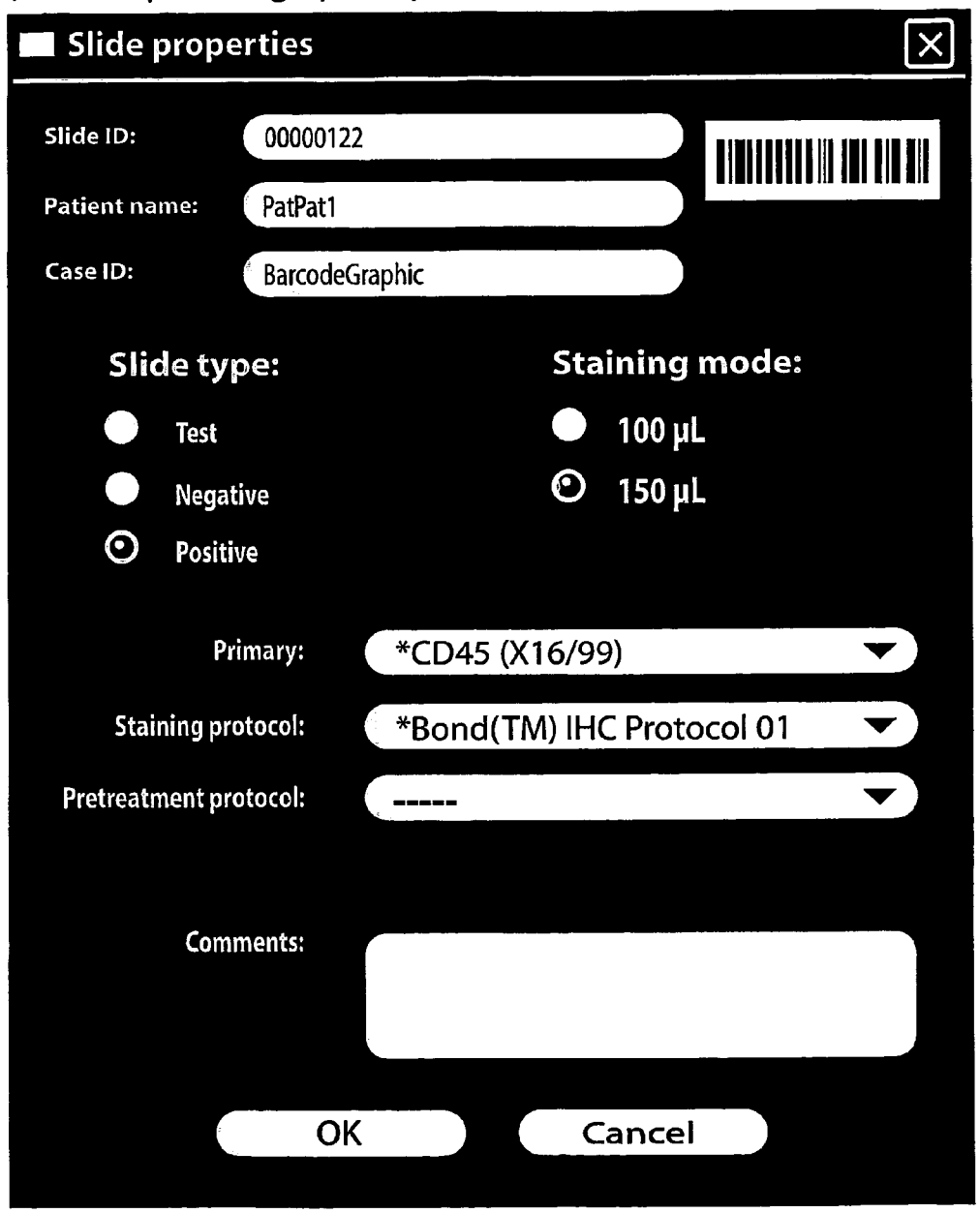
Figure 17:
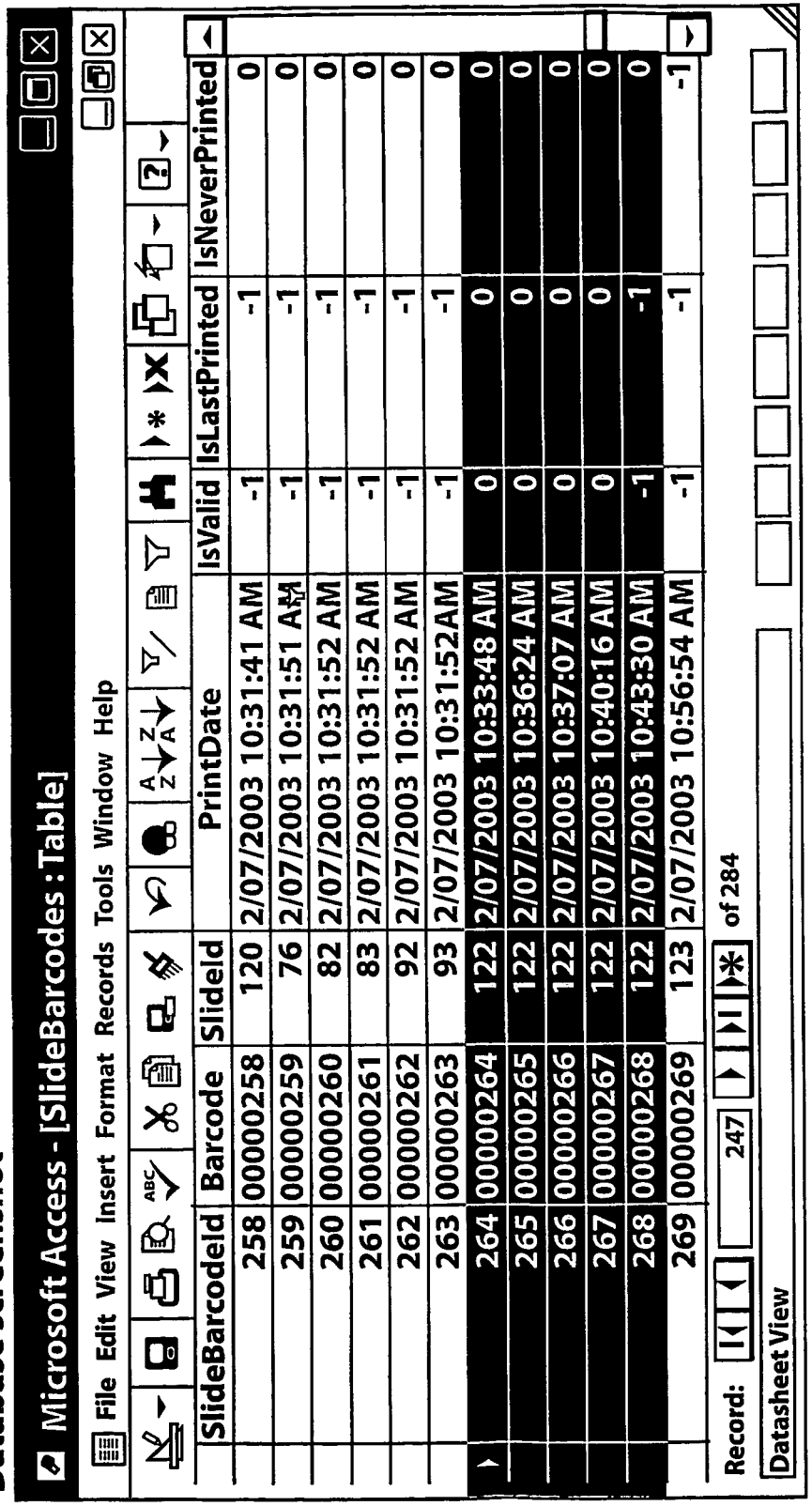

Once the change has been accepted, the Bar Code change (shown in Window 6 of FIG. 15)

The bar code is changed in order to allow the instrument to detect changes in the human readable data printed on the label, and prevent processing of a slide that has incorrect human readable text in relation to the test actually performed. That is, if the bar code was kept the same after the new label was printed, but the new bar code was not put onto the slide, then the human readable data would not reflect the actual test carried out on the slide. In the Bond instrument, if the old label is left on the slide, the instrument knows the bar code is old and will reject the slide.

Another situation not shown in the enclosed figures is when a reagent (Primary or Staining Protocol) is changed, and the changes are accepted, but the slide bar code label is not printed. In such a case, the reagent can be changed as many times as desired, and the bar code will not change until the label is printed. As the bar code label has yet to be printed, the changes in the reagent cannot cause errors, and therefore there is no need to change the bar code. This scenario shows that the bar code is independent of the reagent selection, or reagent data. In Window 13, Barcode 269 shows that the data has been added but the IsNeverPrinted field value is −1. This value tells the controller that the bar code has not been printed.

A database screenshot in Window 13 shows the information stored in the system. On the left is the SlideBarcodeId, which is field from which bar codes are selected sequentially. From SlideBarcodeId, the Barcode column is generated. A separate algorithm takes the USLI and generates the bar code graphic, which appears on the screen and is printed on the label. The next column is SlideId, which is the slide identification number for individual slide to be placed onto the instrument. This number is generated as described earlier. The IsValid field shows a "0" when the bar code is not valid (i.e. has been updated) and a "−1" for the last bar code, which is valid. Similarly IsLastPrinted tells the system which was the last printed bar coded label.

The highlighted fields in the database all relate to the slide opened and described above. As can be seen, an original slideId of 122 was given to the slide and a USLI (referred to in database as SlideBarcodeID) of 264 was associated with the slide. If the bar coded label printed first was read, and not further changes to the reagent had taken place, the computer would have recognised bar code id 264, and looked up the table to get to slide 122. Information about the Primary and Staining Protocol would then be available.

When a change was made to the staining protocol (Window 5 above) the SlideBarcodeId field was updated, with a new number being generated (265) this caused a new bar code to be generated. The bar code generated was independent of the staining protocol selected. This happened several times above, as the old protocols were changed, and each time a new SlideBarcodeId was created. The last SlideBarcodeId created was 268, and the bar code generated from this number is the only bar code that will work, as it is the only one with the IsValid tag at −1. All the rest will produce an error is still on the slide.

The SlideBarcodes table shown in Window 13 is only a subset of the database with other fields such as reagent and protocol information (not shown). These other fields can be cross referenced to provide information on the specific protocol and antibody applied. These fields can be referenced by the SlideID field only. There is no direct connection between the barcode and the reagent information. When a slide, whose details have been previously registered, is loaded into the Bond instrument, the bar code is read. The reader extracts the BarCodeId, from which the slideId number is identified. Using the SlideId number the appropriate reagent or protocol information can be extracted from the database.

From the above it can be seen that the chance of mistakes is minimised, and that the bar code is not related to the staining protocol or primary antibody (reagents) selected.

In one form shown in the figures, the optically readable data is a bar code 17. In another form the optically readable data may be a two dimensional bar code, or alphanumeric characters. In the case of alphanumeric characters, to make the characters easier to read, a font such as E13b may be chosen.

Character strings are able to hold information more densely than a one dimensional bar code and therefore have advantages in certain situations where the size of the label is limited.

When a tray 5 of say, ten slides is loaded into the processing module 2, the reader moves along the tray to each slide position to read the USLI on each slide. Once read, the USLI on a slide 14 is compared to the database in the remote computer 60. The USLI is then correlated with the information in the database, from which a protocol may be extracted and sent to the apparatus. This provides a system whereby, once patient or test data has been entered, the system determines the protocol and reagent to be applied by looking up the remote computer.

Figure 9:
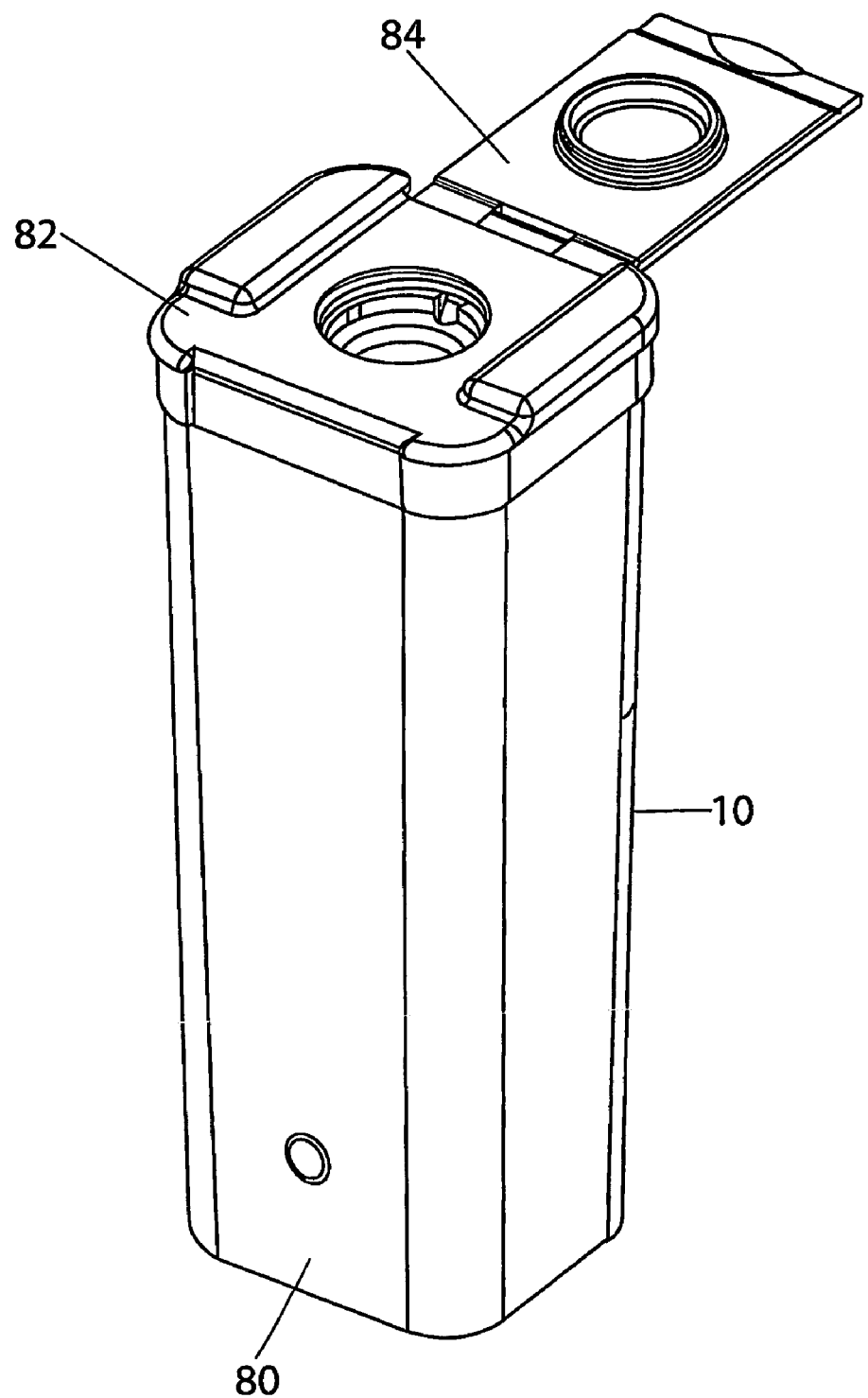
FIG. 9 is a perspective view of a reagent container.

Each free standing (ie not loaded into a reagent tray) reagent container 10, as shown in FIG. 9, has a side surface 80, an upper surface 82 and a lid 84. In FIG. 9 the lid is open but when closed, the lid substantially covers the upper surface 82.

Each reagent container 10 includes a reagent identifier in the form of a label 108. The label 108 includes information that uniquely identifies the reagent container contents. The label 108 is applied during the preparation of the container by the manufacturer. The label 108 in the present embodiment contains a Unique package identifier (UPI) in the form of bar code 110a. Bar code 110c contains information such as reagent type (in this case CD43), reagent batch number, expiry date, and a unique package identifier and additional information as required, however each reagent container must contain the unique container identifier. Bar code 110 a is for an open container and therefore the user is able to enter data relating to the contents of the container. Open containers are supplied empty to allow operators to use their own reagents, and therefore no information is encoded into the bar code 110a for an open container.

Figure 10:
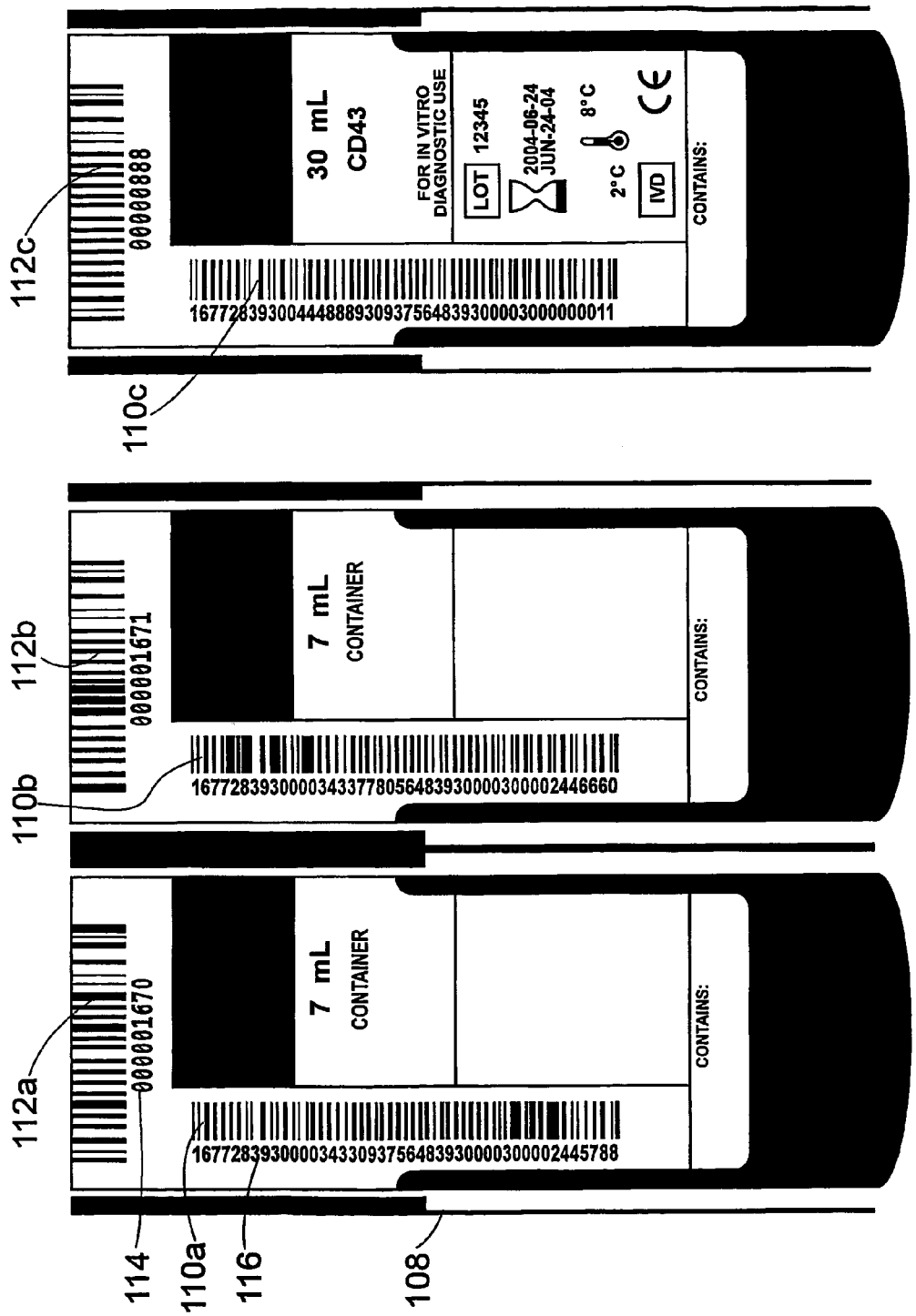
FIGS. 10a-c are examples of free standing reagent container labels having unique reagent container identifiers.

A second identifier in the form of bar code 112a is also shown in FIG. 10a It can be seen that although the label in FIGS. 10a and 10b are identical, they contain different bar codes, so that each container 10 having a label can be uniquely identified.

Each container 10 may optionally also contain a second identifier which just contains the unique identifier, without additional information, as shown in bar code 112a of FIG. 10a. As such, it is possible to register the reagent container either automatically, or manually. In automatic mode, it is possible to send the control system 60 a database of all the unique package identifiers (such as bar code 112a-c) of all the containers in production. By merely scanning a unique package identifier of the containers, the unique package identifier is compared to the database and the reagent type and other information may be extracted and sent to the apparatus. This results in automatic registration of the reagent, including identification of batch no, expiry date etc. This means that straight from delivery, a reagent may be placed into the tray 5 of the processing module 2 without user input.

The unique identification of reagent containers allows the volume of reagent removed from the container to be monitored so that the apparatus can always be sure that sufficient volume remains in the container for the number of tests required in a particular batch. Further, unique identification of each container with additional information allows the apparatus to intelligently use older reagent first if two or more reagent containers of the same type are loaded into the reagent trays.

A second operational method is where the identifier 110c has predetermined fields of information. The identifier 110c may have a unique number field uniquely identifying the reagent container, and another field indicating expiry date, and a third field indicating reagent capacity of container, and a fourth field indicating reagent type. In this way the full information regarding the reagent containers contents could be ascertained by scanning the reagent container. This results in a longer bar code than the previous method but does not require information downloads from the suppliers of the reagent. Additionally, the reagent identifier 110c can be read by the remote controller to identify the contents of the container and its unique identification number, while a second bar code 112c on the container could contain merely the unique identifier on the reagent container to be scanned by the processing module. The unique identifier 112c would be smaller than the reagent bar code 110c due to the removal of information, but would still allow the apparatus to search the control system 60 to identify the reagent container and its contents. Using a shorter unique identifier 112c has benefits in that the apparatus scans the identifier 112c on each reagent container automatically after loading the tray 4 into the processing module 2, and reagent containers may be used a number of times, typically being stored in a refrigerated area when not in use. Reagent containers may also be loaded and unloaded a number of times from trays and therefore after time may suffer some damage. Using a long reagent identifier at registration is advantageous as this registration is undertaken manually, where a number of scans can be made of the long identifier if required. Further, at registration the reagent containers are new and are usually undamaged. At loading, a shorter bar code 112c allows the markings (for example a bar code) to have a larger font. This results in a higher read rate, with less susceptibility to misread from staining and label damage. An additional advantage of using two identifiers is that the label can extend across two planes of the container, such that the shorter label can be placed on the upper surface 82 of the reagent container 10 shown in FIG. 9. If the label 108c is placed along the side 82 of container 10, so that the bar code 110c is wholly along the side 82, and the upper part of the label 108c is folded onto the surface 82, then the bar code 112c will not be visible when the container lid is closed. The processing module does not have the ability to open the containers, but using the two bar codes 110c and 112c it is possible to check whether the lid is open by scanning bar code 112c. If the label 112c is not able to be read then the lid is probably down and will need to be opened prior to running the batch.

If the lid is open about the bar code is unreadable then the identification numbers 114 and 116 can be manually entered into the system to identify the reagent container. That is, the processing module will scan a particular reagent container position in the tray and come up with an error. The user may be prompted to check the container to ensure that there is a container in the position, and that the lid is open. If this is true then the number 114 can be entered into the system and the processing module will query the reagent database on the control system. The control system will then send information relating to the reagent container in that position. This information includes expiry date, batch information and volume remaining in container, allowing reagent management by the instrument.

A third method (not shown) is to provide the reagent container with only a unique identifier and have the details of the reagent container logged manually at registration of the reagent. After that the reagent container is uniquely identified by the apparatus reading the unique identifier.

After loading the slides in the trays, and the unique slide identifiers are read, the apparatus queries the control system for protocol and reagent information. This information is provided from the slide database and the processing module determines whether the correct reagents are loaded, by accessing the information in the memory of the controller regarding reagent containers loaded and scanned. If the correct reagent container is not loaded, or a reagent container has insufficient reagent to complete the required number of tests, the control system may then prompt the user to add more of a particular reagent type. This requires removing one or more trays, adding the required reagent container, and reloading the tray. Reloading the tray prompts the processing module to scan the reagent containers in the tray and record their unique package identifiers. The unique package identifiers are compared with the reagent registration database, and if all reagents are correctly present, the processing module will commence scheduling of the slides.

In this embodiment it is usually not necessary to schedule slides in a single batch or tray, as the slides within a batch are processed sequentially, as all reagents may be adapted to require the same processing time per protocol step. However, if two or more batches are to be run simultaneously, then the sequence of operations by the robot require scheduling so that incubation times are not exceeded. Scheduling is described more fully in Australian Provisional Patent application No 2003900810 by the same applicant.

Once scheduled, the processing module begins processing slides by adding the reagents to the samples as determined by the protocols in the database. At the end of the run, the data relating to each test run on each sample is returned to the control system database and associated with the respective slide, sample and therefore patient. This data does not include results of the test as the analysis system does not review the tested samples for results. However, when the samples are reviewed for results, the full test protocols are available for each slide as data from the processing module 2 is downloaded to control system 60 and associated with each test. This allows verification not only of the protocol selected for the test, but also that the protocol was run within the correct time parameters, and allows verification of batch and processing module used. This is very useful if a batch of reagent was shown to be different to other batches, or an processing module may have had a malfunction (i.e. slides left too long between hydration or overexposure to primary antibody). This verification process offers significantly more detail than merely having a protocol and primary reagent printed on a slide.

An example of order of operation in entering data and running a test is given below.

Step:
1 Operator enters Patient data into control system sample abase
2 Operator enters reagent data/registers reagent containers/kit into control system reagent database
3 Operator prints labels for each slide and places on slides
4 Operator loads slides into tray/s and tray/s into processing module
5 Operator loads reagent containers into trays and then trays or kits into processing module
6 Processing module scans reagent containers upper bar codes to extract UPI
7 Processing module scans slide label bar codes to extract USLI for each sample
8 Processing module sends USLI to control system.
9 Control system extracts protocol and reagent information for each USLI
10 Control system sends protocol and USI information to Processing Module correlated to each slide position
11 Processing module programs dispensation of reagent to each slide from relevant reagent container or kit If more than one slide tray present, schedule slide trays:
12 Processing module runs tests according to schedule
13 Processing module sends information regarding details of tests performed run to control system
14 Control system stores actual test data within sample database As mentioned above the data relating to samples and reagent containers may be downloaded externally from a separate sample or reagent database. Further, one control system (typically a stand alone Personal computer) may control up to 5 processing modules. The personal computer that may be used is a standard personal computer available from a supplier such as Dell Corporation, and would require a hard drive to hold the databases, a network connection to connect to the one or more processing modules, a printer and a scanning device for scanning reagent container information. The software described herein runs on Windows XP operating system and the databases may be relational databases of the SQL type.

While the above has been described with respect to Immunohistochemistry, other processes such as In Situ hybridisation, Fluorescent In Situ hybridisation, Immuno-cytology, all performed on microscope slides, are applicable to the present invention.

The above embodiments of the reagent identifiers allow the operator to use the reagent container on a number of different instruments (provided they all share the same reagent database). Up to five processing modules can share a single control system, and therefore the reagent containers all swappable between these modules.

Figure 4:
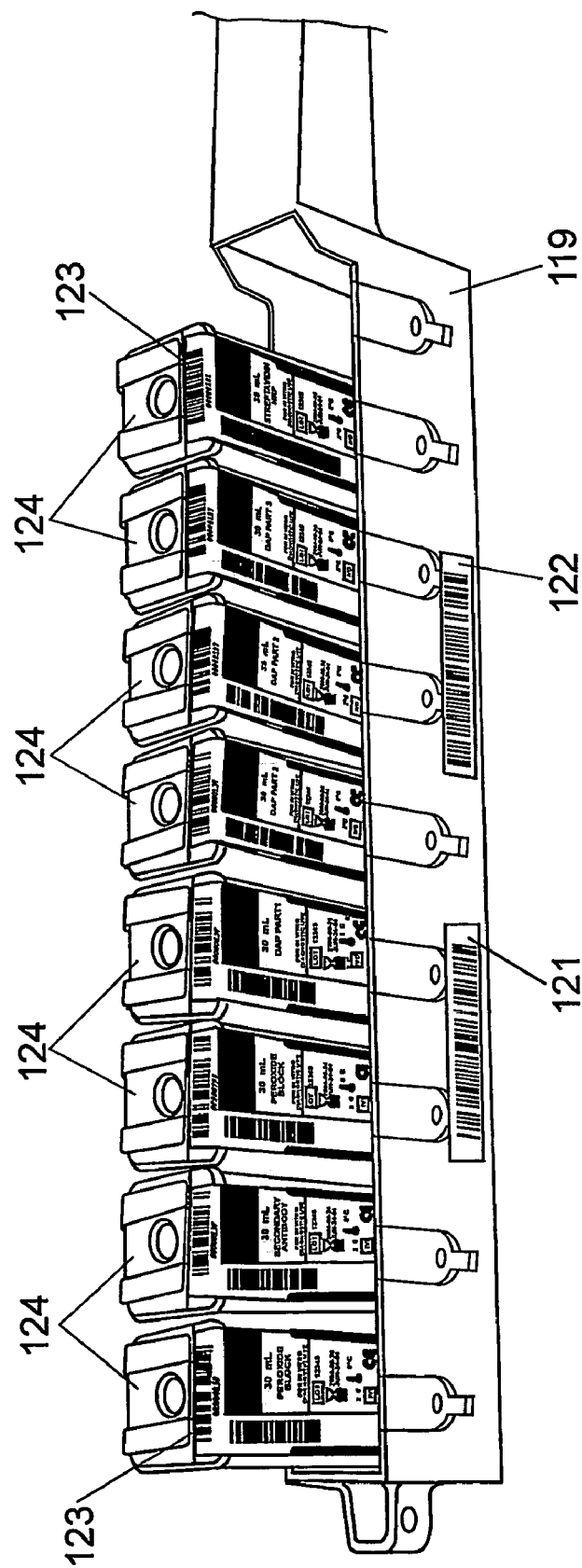
FIG. 4 is a reagent container tray.

A special type of reagent identification system is used in relation to fixed trays. Fixed trays incorporate a set number of reagent containers, and may be used as a detection kit for a particular disease. These kits are shown in FIG. 4. The tray 70 has bar codes on one side, which are able to be read by a hand held scanner 62 connected to the control system 60, schematically shown in FIG. 5. Connection 70 may be a radio link between the scanner and control system, or a wired connection for transferring data. Scanner 62 is typically a handheld bar code scanner.

When the bar codes on the side of the kit are read by the scanner, the control system 60 recognises the contents of the fixed tray. The bar code information on the side of the kit may contain encoded information describing the contents of the kit, such that the control system automatically identifies the contents of the kit. When loaded into the processing module, the bar codes on the top of each container are read, and this information is correlated with the information registered from the side of the fixed tray. The side bar codes incorporate not only the type of reagent, but the relative positions, so it is possible to determine whether the containers are in the correct position by scanning the top bar codes. Typically in a fixed tray such as a detection kit, the containers are physically fixed into the tray and cannot be removed. Another type of kit may employ a range of cancer detection reagents, such as breast cancer. Antibodies included in the kit could include ER, PR, C-erbB2, P53 and Ki67. Typical reagent containers are available from Novocastra Laboratories of Newcastle, UK.

A fixed tray 119 is shown in FIG. 4 having tray bar codes 121 and 122, and nine containers 124. Each container has a bar code label, wherein the top bar code 123 can be seen. To register the product only the tray bar codes 121 and 122 need to be scanned, and after loading into the processing module, only top bar codes 123 are scanned, being unique package identifiers. All top bar codes 123 are scanned to ensure the correct containers are in place, and in the correct order. While the reagent containers are fixed in the tray (by a interlocking mechanism) it maybe possible to force them from the tray to attempt to use them in a different system, so verification is useful.

Figure 3:
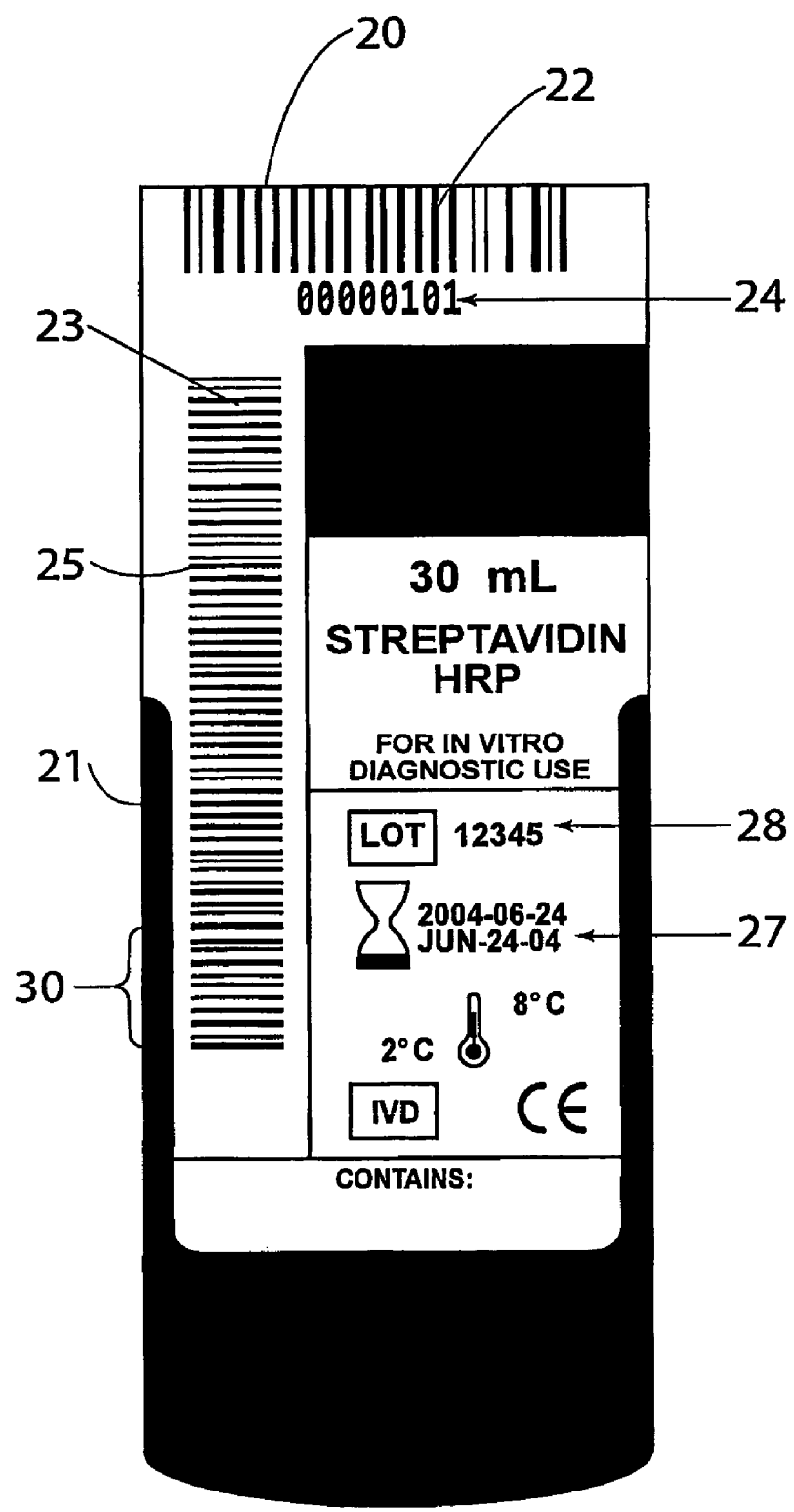
FIG. 3 is a plan view of a tag on a free standing reagent container.

FIG. 3 shows another example of a reagent container. The tag 21 in fact carries two types of barcode 22,23. The unique identifier 20 which is shown represents an eight-digit number which identifies the actual reagent container 10 itself. An alphanumeric representation 24 of the identifier 20 appears beneath the barcode 22.

The second barcode 23 is in the form of a sequence of characters 25 which provide more detailed information relating to the reagent carried within the container 10. The sequence 25 may include thirty characters, which represent data such as product name 26, expiry date 27, lot number 28, serial number, and the like. The sequence 25 also includes embedded identifier code 30 to allow the reagent information to be cross-correlated with the identifier code 20 in the first barcode 22. Again, alphanumeric and pictorial representations of the type of information carried by the sequence of characters is illustrated adjacent the second barcode.

The above embodiments also allow the registration of reagent and subsequent storage, as the instrument can tell which reagents should be used first as expiry data is captured.

The invention claimed is:

1. An analysis system comprising:
   an apparatus for applying reagents to tissue samples mounted on slides, the apparatus having:
   a first reader that reads a unique identifier relating to at least one of reagents prior to the reagents being added to the system and slides prior to the slides being loaded into the system;
   a moveable second reader that moves to read unique identifiers applied to the slides after slides have been loaded onto the apparatus, and that moves to read unique identifiers applied to reagent containers after reagent containers have been loaded, and
   a controller which receives input from the first reader regarding at least one of reagents being added to the system and slides being loaded into the system and receives input from the second reader as slides are analyzed by the system,
   wherein the controller, after input from the second reader, applies reagents from the reagent containers to the slides in accordance with separately input test protocol information.

2. The system of claim 1, wherein the first reader is a handheld scanning device and the second reader is mounted to a robot arm.

3. The system of claim 1, wherein the reagent container has two identifiers, and wherein a first identifier is readable by the first reader and contains reagent volume information, and a second identifier is readable by the second moveable reader and contains unique identifier information.

4. The system of claim 3, wherein the first identifier includes additional information including one or more of the following: reagent container capacity, expiry date and reagent batch number.

5. The system of claim 1, wherein the first reader reads a unique identifier relating to a slide or a reagent container prior to the slide or reagent container being loaded onto the apparatus.

6. The system of claim 1, wherein the first reader reads a unique identifier relating to a slide prior to the slide being loaded onto the apparatus.

7. The system of claim 1, wherein the first reader reads a unique identifier relating to a reagent container prior to the reagent container being loaded onto the apparatus.

8. The system of claim 1, wherein the first reader reads a unique identifier on a side of a fixed tray, the tray comprising a plurality of reagent containers.

9. The system of claim 8, wherein the fixed tray is a detection kit for a particular disease.

10. The system of claim 8, wherein the fixed tray has the unique identifier on the side of the fixed tray, and each of the plurality of containers has a unique identifier.

11. The system of claim 8, wherein when the first reader reads the unique identifier on the side of the fixed tray, the control system recognizes the contents of the plurality of containers in the fixed tray.

* * * * *

UNITED STATES PATENT AND TRADEMARK OFFICE
CERTIFICATE OF CORRECTION

PATENT NO. : 8,396,669 B2
APPLICATION NO. : 10/546458
DATED : March 12, 2013
INVENTOR(S) : Cocks et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1625 days.

Signed and Sealed this
First Day of September, 2015

Michelle K. Lee
*Director of the United States Patent and Trademark Office*